United States Patent
Freudiger

(10) Patent No.: US 7,597,707 B2
(45) Date of Patent: Oct. 6, 2009

(54) PEDICLE SCREW WITH A CLOSURE DEVICE FOR THE FIXING OF ELASTIC ROD ELEMENTS

(75) Inventor: Stefan Freudiger, Brewgarten (CH)

(73) Assignee: Spinelab AG, Zug (CH)

( * ) Notice: Subject to any disclaimer, the term of this patent is extended or adjusted under 35 U.S.C. 154(b) by 0 days.

(21) Appl. No.: 10/965,841

(22) Filed: Oct. 18, 2004

(65) Prior Publication Data
US 2005/0096659 A1     May 5, 2005

(30) Foreign Application Priority Data
Oct. 31, 2003   (EP)   ................. 03405786

(51) Int. Cl.
*A61B 17/70*   (2006.01)
(52) U.S. Cl. ............ 606/254; 606/255; 606/261; 606/265
(58) Field of Classification Search ......... 606/61, 606/72–73
See application file for complete search history.

(56) References Cited

U.S. PATENT DOCUMENTS

| | | | | |
|---|---|---|---|---|
| 4,448,191 A * | 5/1984 | Rodnyansky et al. | ......... | 606/61 |
| 5,257,993 A * | 11/1993 | Asher et al. | ......... | 606/61 |
| 5,380,326 A * | 1/1995 | Lin | ......... | 606/61 |
| 5,403,316 A * | 4/1995 | Ashman | ......... | 606/61 |
| 5,496,321 A | 3/1996 | Byrd, III et al. | | |
| 5,562,663 A * | 10/1996 | Wisnewski et al. | ......... | 606/61 |
| 6,110,172 A * | 8/2000 | Jackson | ......... | 606/61 |
| 6,139,549 A * | 10/2000 | Keller | ......... | 606/61 |
| 6,302,888 B1 * | 10/2001 | Mellinger et al. | ......... | 606/73 |
| 6,565,565 B1 * | 5/2003 | Yuan et al. | ......... | 606/61 |
| 6,565,566 B1 * | 5/2003 | Wagner et al. | ......... | 606/61 |
| 6,585,737 B1 * | 7/2003 | Baccelli et al. | ......... | 606/61 |
| 6,786,903 B2 * | 9/2004 | Lin | ......... | 606/23 |
| 6,843,791 B2 * | 1/2005 | Serhan | ......... | 606/61 |
| 6,896,677 B1 * | 5/2005 | Lin | ......... | 606/61 |
| 6,911,030 B1 * | 6/2005 | Vanacker et al. | ......... | 606/61 |
| 6,966,910 B2 * | 11/2005 | Ritland | ......... | 606/61 |
| 6,989,011 B2 * | 1/2006 | Paul et al. | ......... | 606/61 |
| 2003/0004511 A1 | 1/2003 | Ferree | | |
| 2003/0125742 A1 | 7/2003 | Yuan et al. | | |

FOREIGN PATENT DOCUMENTS

DE           19534136 A1      3/1996

(Continued)

*Primary Examiner*—Eduardo C Robert
*Assistant Examiner*—Mary Hoffman
(74) *Attorney, Agent, or Firm*—Jacobson Holman PLLC

(57) ABSTRACT

A pedicle screw with a closure device including a seat element and a closure cap for quick closure of the seat element of the pedicle screw. An elastic rod element inserted therein in the seat recess, which element serves to stabilize a vertebral column, is held in a form-locking way. The closure cap of the closure device has the function of a cross-brace, and can transfer the forces absorbed by it from the rod element to the pedicle screw. Disposed on the closure cap with a holding recess are engagement elements which, during insertion of the closure cap, automatically lock in place in a stable position in the seat element provided with a U-shaped seat recess. The seat recess and the holding recess preferably have a ridged or grooved structure corresponding to the rod element used.

5 Claims, 5 Drawing Sheets

FOREIGN PATENT DOCUMENTS

| | | |
|---|---|---|
| DE | 19540180 A1 | 5/1996 |
| DE | 19951145 A1 | 5/2001 |
| FR | 2780269 | 12/1999 |
| WO | WO95/01132 | 1/1995 |
| WO | WO03/015648 | 2/2003 |

* cited by examiner

PEDICLE SCREW WITH A CLOSURE DEVICE FOR THE FIXING OF ELASTIC ROD ELEMENTS

FIELD OF THE INVENTION

This invention relates to orthopedic implants, and more specifically to a pedicle screw with a closure device, comprising a seat element with a U-shaped seat recess, into which recess a closure cap is insertable for quick closure of the seat element of the pedicle screw, to receive an elastic rod element, placeable therein, which serves to stabilize a vertebral column, and to hold it with the closure device via a holder. It serves for quick, secure and simple fastening and connection during spinal surgery.

BACKGROUND OF THE INVENTION

In the state of the art there is a wide selection of pedicle screws with closure devices having, as a rule, a receiving part with a U-shaped recess for receiving a rod, which recess has between its free arms an internal threading for accepting a screw for fixing the rod.

U.S. Pat. No. 5,496,321 describes a pedicle screw with an anchoring means. This product has the disadvantage, however, that the anchoring means has to be inserted in the screw head in the direction of the rod, which, in the case of small radii of curvature of the rod, can lead to considerable difficulties under operating conditions.

U.S. published patent application No. 2003/0004511 describes a pedicle screw system, whose receiving arms for a rod are connected with a hinge. After receiving the rod, the receiving arms are provided with a closure cap or a closure yoke, which press the arms together and hold the rod firmly. To put on the closure cap or yoke, the arms of the head of the pedicle screw have to be pressed together, and at the same time the closure piece has to be pushed in the rod direction or turned, or repetitively the closure yoke has to be pushed in the rod direction or turned, or respectively the closure yoke has to be hung, requiring not only considerable skill on the part of the operator, but, depending upon the embodiment, also a special instrument.

SUMMARY OF THE INVENTION

The present invention therefore has the object of providing a pedicle screw with a closure device which ensures the transmission of forces from the rod to the screw on the open side, and prevents the rod from being able to slip out backwards, and permits a secure and quick closure of the seat of the rod in the pedicle screw in order to firmly hold this rod therein. Furthermore, the closure device must also be removable again.

It has been found that these objects can be achieved through a closure device which carries out the function of a cross-brace that engages on the rod in a provided grooved structure and which transmits forces thus absorbed in lengthwise direction of the rod to the flanks, also provided with grooves, of the open seat of the pedicle screws. To solve the technical problem, the closure device must further comprise an engagement means (e.g. two hooks). For this purpose, the closure cap must be elastically maneuverable, so that it itself locks into place (hooks in) upon insertion in the seat of the pedicle screw. Furthermore, for a quick and secure removal again, respective means must be available, where a corresponding instrument, preferably a universal instrument, can engage.

The subject matter of the present invention is thus a pedicle screw with a closure device, comprising a seat element with a U-shaped seat recess, into which recess a closure cap is insertable for quick closure of the seat element of the pedicle screw, to receive an elastic rod element, placeable therein, which serves to stabilize a vertebral column, and to hold it with the closure device via a holder, wherein the rod element, the U-shaped seat recess of the seat element and the closure cap each have a ridged or grooved surface structure, corresponding to one another, and which surface structures come into engagement with one another in a form-locking way at the respective places of contact such that the closure cap carries out the function of a cross-brace and the forces which are active in lengthwise direction of the rod element are thereby transmittable to the pedicle screw.

The pedicle screw with the closure device according to the invention is useful for quick and secure closure and connection of an elastic rod element to a pedicle screw with a simultaneous transmission of forces from the rear rod side to the flanks of the pedicle screw. The closure cap provided for the closure device is advantageously made of a biocompatible synthetic material, preferably of polyurethane of medical grade quality which can be processed through injection molding. To insert the closure cap in the matching holding element, the hooks provided on the closure cap automatically lock into place in the matching depressions in the arms of the closure device at the head of the pedicle screw, as soon as they are in the correct position. Further provided are means making possible a simple removal of these closure devices, should this be necessary during the ongoing, or a later, operation. A kinematic reversal of hooks and depressions is likewise possible and should be covered by the definition of the present invention, although the geometry of the depressions must be adapted, which does not present an insolvable problem for one skilled in the art.

At least one, preferably two, engagement projections provided in the seat recess serve to prefix the rod element in the seat element before the closure cap is inserted, it being possible for the rod element to be held partially as well as completely in the seat element in a form-locking way such that, for position correction, a simple removal and reinsertion of the rod element is possible during an operation. For this purpose both the rod element and the seat recess have a grooved/ridged structure, fitting into one another, in transverse direction with respect to the rod element. A co-operation of the engagement projection or projections with the mentioned form-locking structure permits a prefixing in lengthwise and crosswise direction with respect to the rod element. For this purpose, the grooved structure in the interior of the seat recess is preferably extended until the ends of its arms. The mentioned engagement projections may be positioned such that, in engaged state, they exercise a slight pressure on the rod element, or penetrate into the rod in a form-locking way, it also being possible to provide for a slight offsetting. In closed state, the closure device with the mentioned features also enables absorption of torsional forces exerted by the rod element.

BRIEF DESCRIPTION OF THE DRAWINGS

The invention is illustrated in the attached figures with reference to examples, different features being explained with reference to their purpose and their function.

DETAILED DESCRIPTION OF THE PREFERRED EMBODIMENTS

Figure 1:
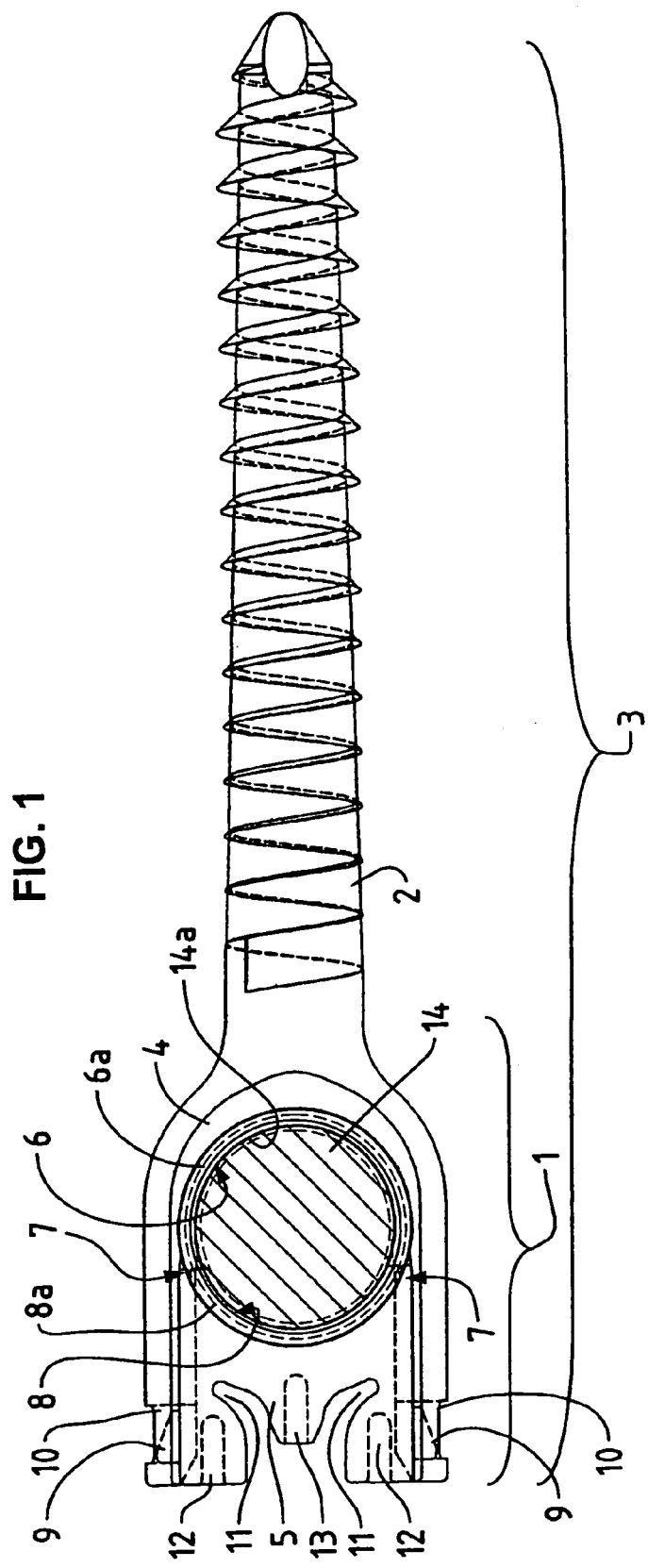
FIG. 1 shows a typical pedicle screw with seat element and closure cap according to the invention.

FIG. 1 shows a typical embodiment of the closure device 1 according to the invention. Together with a threaded part 2, it forms a pedicle screw 3, the closure device representing its head. The seat element 4, consisting of two arms, with its U-shaped seat recess 6, serves to receive an elastic rod element 14, whereby an engagement projection 7 serves to prefix the rod element in such a way that the rod element can be removed again from a pedicle screw implanted on a vertebra, without any difficulty, during an operation, if necessary. The easy locking into place is caused by the elasticity of the rod element and/or of the U-shaped holding recess of the holding element. The rod element 14, the seat recess 6 and the holding recess 8 have a structure fitting into one another, e.g. ridges or grooves 8a, 6a, preferably in transverse direction with respect to the rod element. In the embodiment shown, for optimization of a prefixing and for early longitudinal positioning, the grooves or ridges in the seat recess on its arms are extended to the ends. By means of the features mentioned, an optimal transmission of forces from the rod element 14 to the pedicle screw 3 is produced, whereby the closure cap, acting as a cross-brace (which will be described more closely in the following) engages with its holding recess 8 in the rod element 14 in a form-locking way.

If the position of the rod is correct, the closure cap 5 is placed in the seat element 4. Used to do this is an adapted instrument, such as a universal screw driver, on which the closure cap can be put, via the recesses 11, 13, and the closure cap can be inserted in the seat recess in correct position in an exact fitting way, with an automatic locking into place. For removal or respectively correction, a further instrument is used, e.g. universal tongs, having engagement projections for insertion in the recesses 12. The closure cap has engagement elements (hooks) 9 on both sides which, with deformation of the closure cap in the region of the engagement recesses 10, serve the locking into place. If the closure cap 5 is supposed to be removed again from the seat element 1, it is removed by means of the mentioned universal tongs. Through the engagement of the tongs in the recesses 12 and slight pressing together of the tongs, the elastic closure cap is pressed, the engagement elements 9 being pulled out of the engagement recesses 10 and the closure cap being able to be removed again from the seat recess 6.

Figure 2:
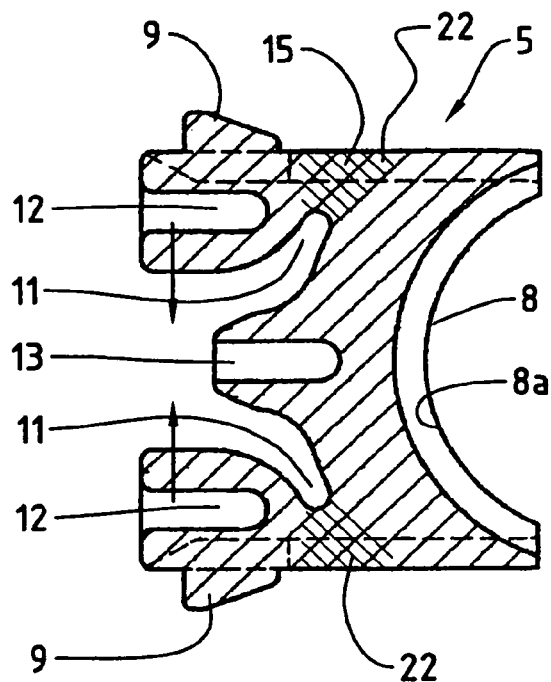
FIG. 2 shows a side elevation of the closure cap in the pedicle screw according to the invention represented in FIG. 1.

FIG. 2 shows a sectional drawing of the closure cap of the closure device according to the invention shown in FIG. 1. The reference numerals correspond to the meanings indicated for FIG. 1. In addition, the resilient deformation regions 15 are shown which permit a compression of the closure cap in the upper part with said special tool in the direction of the arrow in such a way that the mutual spacing of the engagement elements (hooks) is reduced, which causes an automatic locking into place and also a removal of the closure cap from the seat recess by disengagement.

On the two lateral flanks the surfaces are also structured, and are provided with grooves or ridges 22. In the state of being inserted in the U-shaped seat recess 6, as is shown in FIG. 1, these ridges or grooves 22 engage in the corresponding surface structure of the seat recess 6 formed by the arms. Thus a form-locking connection is created here too.

A transmission of the forces acting in longitudinal direction in the rod element 14 thus takes place in the region where the rod element 14 is in contact with the seat recess 6, in a form-locking way directly on the pedicle screw 3. In the area of contact of the rod element 14 with the closure cap 5, the transmission of forces takes place in a form-locking way to the closure cap 5, acting as a cross-brace, from where, once again, a form-locking transmission occurs to the arms of the U-shaped seat recess 6 of the pedicle screw 3. An optimal force transmission is thereby ensured, in particular also of bending forces, since the rod element 14 is completely surrounded.

Figure 3:
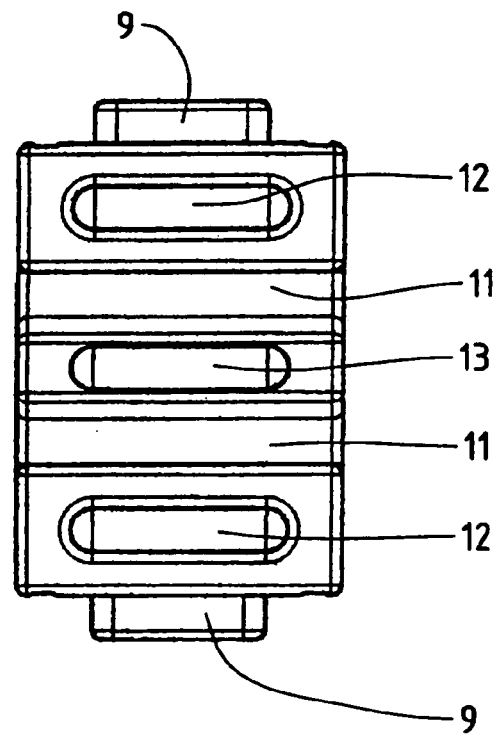
FIG. 3 is a view from above of the closure cap shown in FIG. 2.

FIG. 3 is a view of the closure cap from above, the meaning of the reference numerals once again corresponding to the above definitions.

Figure 4:
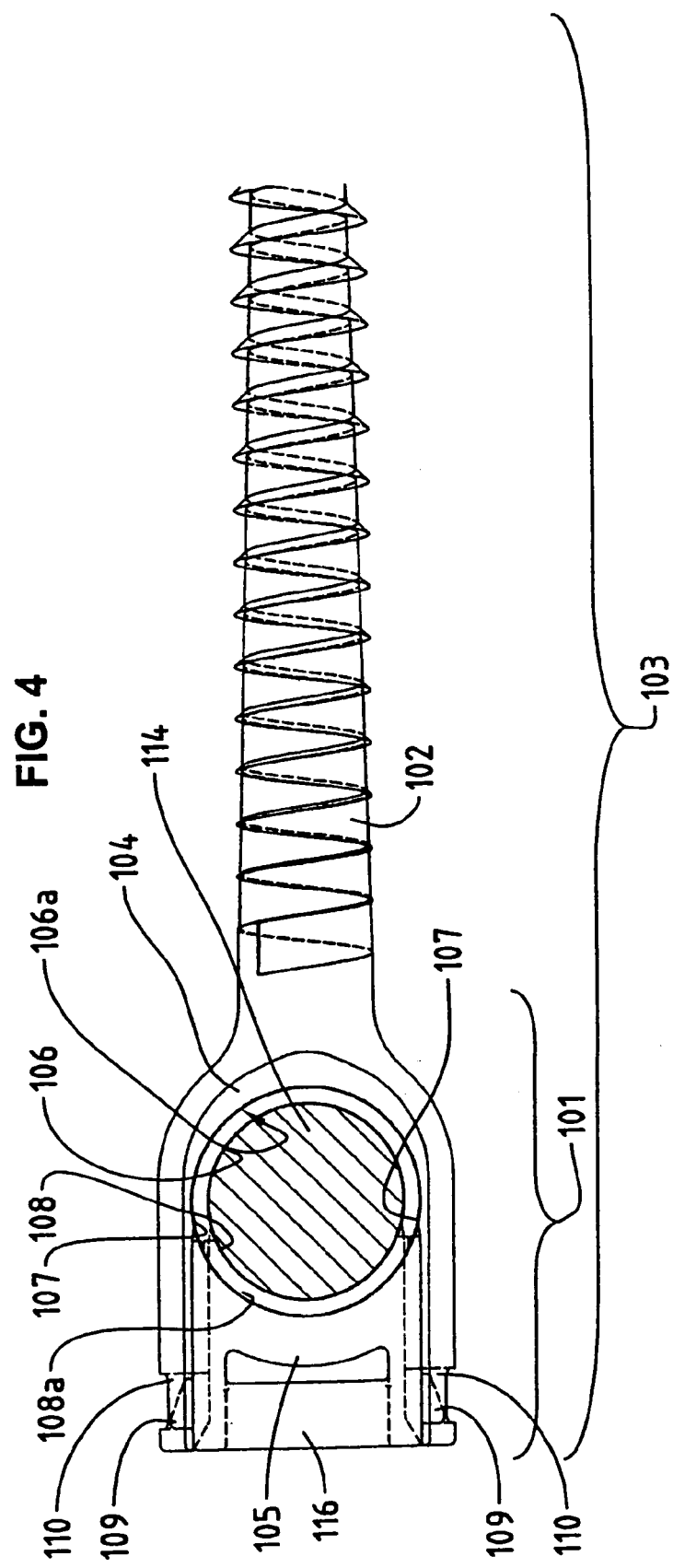
FIG. 4 is a further embodiment of a pedicle screw with seat element and closure cap according to the invention.

FIG. 4 shows an alternative embodiment of the closure device 101 according to the invention. Together with a threaded part 102, it forms a pedicle screw 103. The seat element 104 with its U-shaped seat recess 106 serves to receive an elastic rod element 114, whereby an engagement projection 107 serves the purpose of a prefixing of the rod element 114 in such a way that the rod element can be removed again from a pedicle screw implanted on a vertebra without any difficulty during an operation, if necessary. The rod element 114, the seat recess 106 and the holding recess 108, as well as the two lateral flanks of the closure cap 105 have here too a structure fitting into one another, e.g. ridges or grooves 106a, 108a, 122, preferably in transverse direction, in order to achieve an optimal transmission of forces.

If the position of the rod element is correct, the closure cap 105 is inserted into the seat element 104. The closure cap has hooks or engagement elements 109 on both sides, which, with deformation of the closure cap in the region of the engagement recesses, serve engagement in the engagement recesses 110 of the seat element 101. A buckled crosspiece 116, in engaged state, furthers the pressure on the hooks 109 and thus the firm seating of the closure cap.

Figure 5:
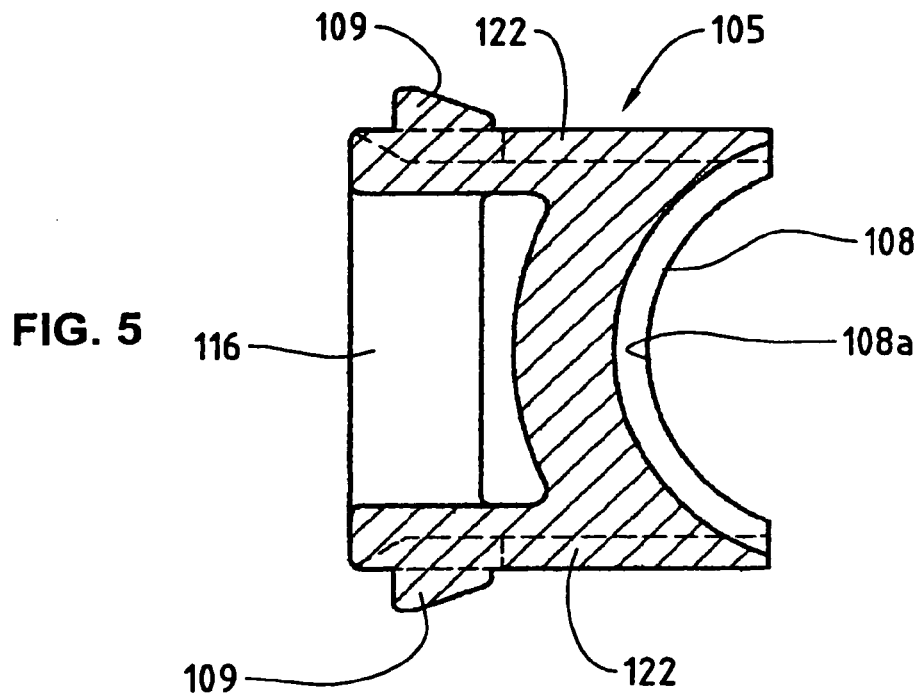
FIG. 5 is a side elevation of the closure cap of the pedicle screw shown in FIG. 4.

FIG. 5 shows a sectional drawing of the closure cap of the closure device according to the invention shown in FIG. 4. The reference numerals correspond to the meanings indicated for FIG. 4.

Figure 6:
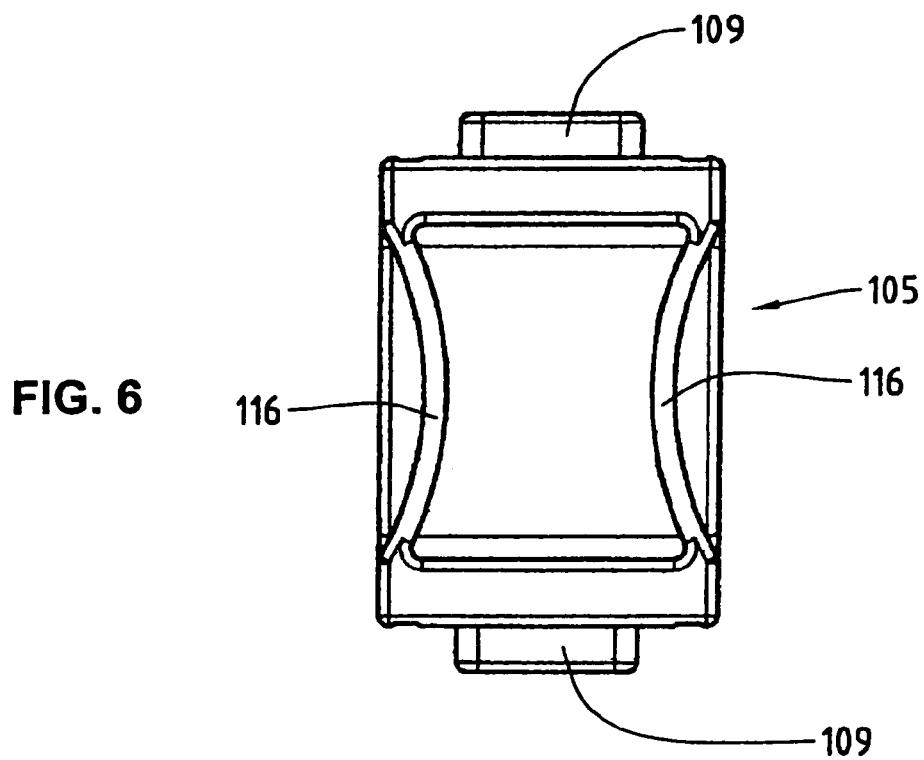
FIG. 6 is a view from above of the closure cap shown in FIG. 5.

FIG. 6 is a view of the closure cap from above, the meaning of the reference numerals corresponding once again to the above definitions.

Figure 7:
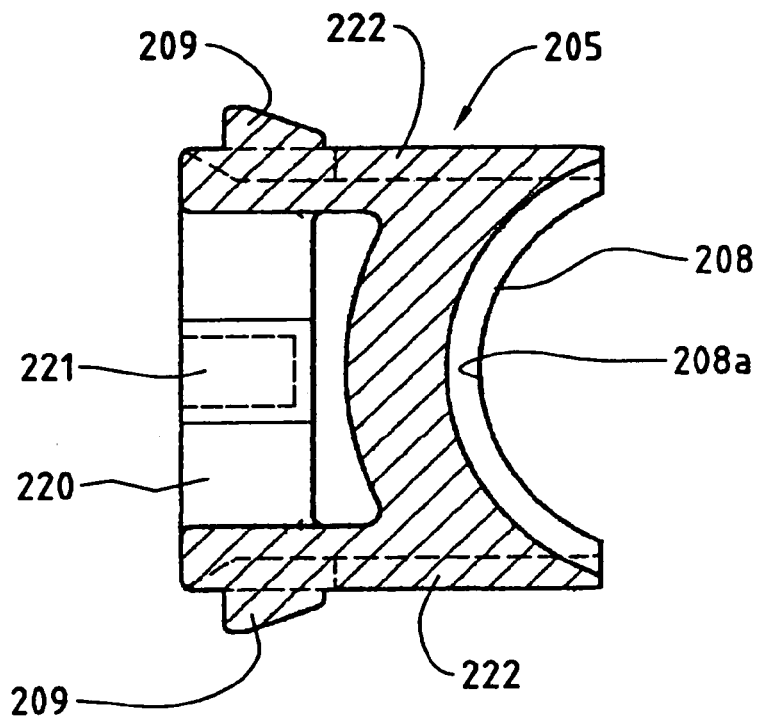
FIG. 7 is a side elevation of an alternative closure cap with an S-loop.

FIG. 7 shows a sectional drawing of an alternative closure cap for a closure device according to the invention. The reference numerals have the following significance: 205 the closure cap; 208 the holding recess; 208a ridges/grooves; 209 the hooks; and 222 ridges/grooves. 220 designates an S loop with a blind hole 221 for insertion of a screwdriver, a turning movement causing a moving together of the hooks 209 and thus a release of the closure cap.

Figure 8:
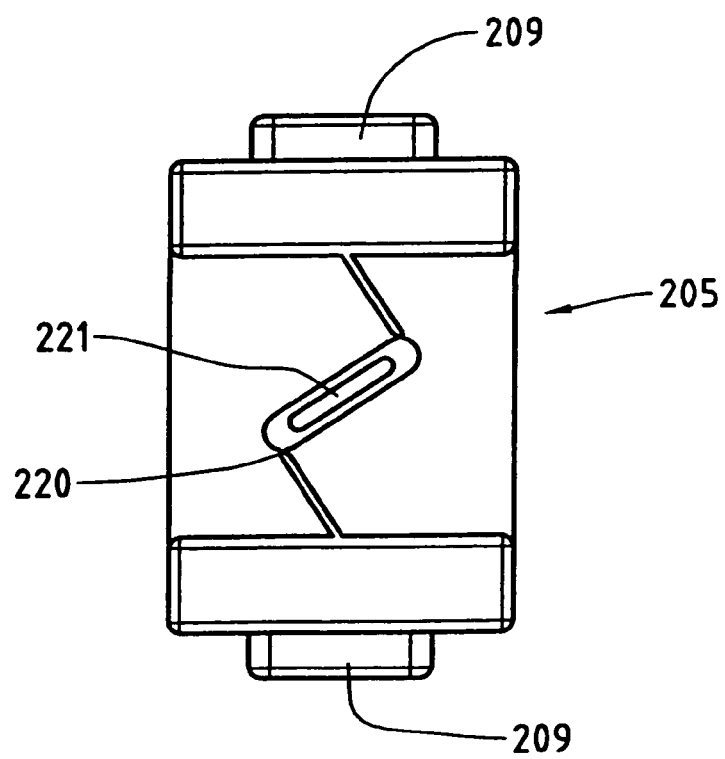
FIG. 8 is a view from above of the closure cap shown in FIG. 7.

FIG. 8 is a view from above of the alternative closure cap according to FIG. 7, the significance of the reference numerals corresponding once again to the above definitions.

The invention claimed is:

1. A pedicle screw assembly comprising
a closure device having a seat element with a U-shaped seat recess, the U-shaped recess including grooves or ridges,
an elastic rod element having grooves or ridges, the grooves or ridges of the elastic rod element extending in a transverse direction with respect to a lengthwise direction of the elastic rod element,
an elastic closure cap having grooves or ridges, the elastic closure cap being inserted internally of the U-shaped seat recess for quick closure of the seat element and thereby forming a substantially circumferential enclosure between the U-shaped seat recess and the closure cap to receive the elastic rod element placeable within the substantially circumferential enclosure between the U-shaped seat recess and the closure cap for stabilizing a vertebral column and to hold the surrounded and engaged elastic rod element with the closure device,
holder elements of the elastic closure cap securing the closure cap in the seat element,
the grooves or ridges of the U-shaped seat recess of the seat element and the grooves or ridges of the elastic closure cap each corresponding to one another, and the respective grooves or ridges engaging one another in a form-locking way at places of contact such that the elastic rod element carries out the function of a cross-brace and forces which are active in a lengthwise direction of the elastic rod element along a longitudinal axis of the elastic rod element are thereby transmittable to the closure device,
the respective grooves or ridges of the U-shaped seat recess of the seat element and the elastic closure cap being aligned transversely to the lengthwise direction of the elastic rod element, and the grooves or ridges in the seat recess being extended until ends of two arms formed by the seat element and the respective grooves or ridges in the seat recess fitting into the grooves or ridges in the elastic rod element.

2. The pedicle screw assembly according to claim 1, wherein the holder elements include engagement elements disposed on the closure cap and matching receiving openings in the U-shaped seat recess automatically locking the engagement elements into place in the receiving openings during placement of the closure cap in the seat element.

3. The pedicle screw assembly according to claim 2, wherein the engagement elements include at least two oppositely directed hooks, resiliently disposed relative to one another so that the closure cap is able to engage in the receiving openings provided on the two arms of the seat element in the inserted state.

4. The pedicle screw assembly according to claim 3, wherein the closure cap is provided with depressions or projections next to the resiliently disposed hooks, the depressions or projections are engaged by an instrument in a central depression in the closure cap, and a separation between the hooks is reduced through pressing together of the depressions or projections, which, upon disengagement from the receiving openings, allows a removal of the closure cap from the seat element.

5. The pedicle screw assembly according to claim 1, wherein at least one engagement projection is provided in the U-shaped seat recess at a position where an engagement of the elastic rod element is performed in such a way that upon insertion a correctable pre-fixing with torsion blocking is achieved.

* * * * *